United States Patent
Minamino et al.

(10) Patent No.: US 9,670,516 B2
(45) Date of Patent: Jun. 6, 2017

(54) METHOD OF PRODUCING SUGAR LIQUID

(71) Applicant: Toray Industries, Inc., Tokyo (JP)

(72) Inventors: Atsushi Minamino, Kamakura (JP); Hiroyuki Kurihara, Kamakura (JP); Katsushige Yamada, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 14/406,841

(22) PCT Filed: Jun. 11, 2013

(86) PCT No.: PCT/JP2013/066014
§ 371 (c)(1),
(2) Date: Dec. 10, 2014

(87) PCT Pub. No.: WO2013/187385
PCT Pub. Date: Dec. 19, 2013

(65) Prior Publication Data
US 2015/0140606 A1 May 21, 2015

(30) Foreign Application Priority Data
Jun. 12, 2012 (JP) ................ 2012-132729

(51) Int. Cl.
| | |
|---|---|
| C12P 1/00 | (2006.01) |
| C12P 19/14 | (2006.01) |
| C12P 7/10 | (2006.01) |
| C12P 7/56 | (2006.01) |
| C13K 1/02 | (2006.01) |
| C12P 19/02 | (2006.01) |
| C13K 1/04 | (2006.01) |
| C12P 7/14 | (2006.01) |
| C13K 13/00 | (2006.01) |

(52) U.S. Cl.
CPC ........... *C12P 19/14* (2013.01); *C12P 7/10* (2013.01); *C12P 7/14* (2013.01); *C12P 7/56* (2013.01); *C12P 19/02* (2013.01); *C13K 1/02* (2013.01); *C13K 1/04* (2013.01); *C13K 13/002* (2013.01); *C12P 2201/00* (2013.01); *Y02E 50/16* (2013.01)

(58) Field of Classification Search
USPC .......................................................... 435/41
See application file for complete search history.

(56) References Cited

U.S. PATENT DOCUMENTS

| | | | |
|---|---|---|---|
| 7,442,359 B2 | 10/2008 | Van Groenestijn et al. | |
| 2007/0148750 A1 | 6/2007 | Hoshino et al. | |
| 2009/0173339 A1* | 7/2009 | Heikkila | B01D 61/027 127/55 |
| 2011/0250637 A1 | 10/2011 | Kurihara et al. | |

FOREIGN PATENT DOCUMENTS

| | | |
|---|---|---|
| EP | 1 306 442 | 5/2003 |
| JP | 62-201606 | 9/1987 |
| JP | 5-58601 | 3/1993 |
| JP | 2008-529946 | 8/2008 |
| JP | 2011-223975 | 11/2011 |
| WO | 2007/097260 | 8/2007 |
| WO | 2010/067785 | 6/2010 |
| WO | 2012/077698 | 6/2012 |
| WO | 2012/100187 | 7/2012 |

OTHER PUBLICATIONS

Liu, Shije et al. Membrane Filtration: Concentration & Purification of Hydrolyzates from Biomass. Journal of Biobased Materials and Bioenergy. vol. 2, (2008). pp. 121-134.*
Taherzadeh, Mohammed. Pretreatment of Lignocellulosic Wastes to Improve Ethanol and Biogas Production: A Review. International Journal of Molecular Science. (2008). vol. 9, pp. 1621-1651.*
Jarusutthirak, Chalor. Factors Affecting Nanofiltration Performances in Natural Organic Matter Rejection & Flux Decline. Separation and Purification Technology 58. (2007). pp. 68-75.*
Liu (Membrane Filtration: Concentration & Purification of Hydrolyzates from Biomass, 2008).*
Taherzadeh (Pretreatment of Lignocellulosic Wastes to Improve Ethanol and Biogas Production: A Review, 2008).*
Jarusutthirak (Factors Affecting Nanofiltration Performances in Natural Organic Matter Rejection & Flux Decline, 2007).*
Schell, D.I.; Farmer, 1.; Newman, M.; McMillan, 1.D. Dilute-sulfuric acid pretreatment of corn stover in pilot-scale reactor: Investigation of yields, kinetics, and enzymatic digestibilities of solids. Appl. Biochem. Biotechnol. 2003.*
Restolho, et al., "Sugars and lignosulphonates recovery from eucalyptus spent sulphite liquor by membrane processes," *Biomass and Bioenergy*, 2009, vol. 33, pp. 1558-1566.
M. Furuichi, et al., "Studies on enzymic saccharification, enzyme recovery by UF and sugar concentration by RO membranes," *World Congress 3 of Chemical Engineering*, 1986, pp. 255-257.
A. Aden, et al., "Lignocellulosic Biomass to Ethanol Process Design and Economics Utilizing Co-Current Dilute Acid Prehydrolysis and Enzymatic Hydrolysis for Corn Stover," NREL Technical Report, Jun. 2002.
T. Yanagida, "Energy and economic evaluation for ethanol production of non sulfuric acid pretreatment method from rice straw," *Journal of Japan Society of Energy and Resources*, vol. 30, No. 5, p. 8, abstract only.
AIST Today, July issue, 2009, p. 14-15 with brief English summary.
Supplementary European Search Report dated Jan. 8, 2016 of corresponding European Application No. 13804556.2.
Notification of Reasons for Refusal dated Apr. 11, 2017, of corresponding Japanese Application No. 2013-535973, along with an English translation.

\* cited by examiner

*Primary Examiner* — Scott Long
*Assistant Examiner* — Nghi Nguyen
(74) *Attorney, Agent, or Firm* — DLA Piper LLP (US)

(57) ABSTRACT

A method of producing a sugar liquid from cellulose-containing biomass includes (1) to (4): (1) subjecting a cellulose-containing biomass to a dilute sulfuric acid treatment and thereafter separating the treated cellulose-containing biomass into a dilute sulfuric acid-treated liquid and a cellulose-containing solid content; (2) adding a cellulase to the cellulose-containing solid content to hydrolyze the cellulose and thereafter obtaining a sugar liquid; (3) filtering the dilute sulfuric acid-treated liquid through a nanofiltration membrane at pH 2.5 or lower to thereby separate a sugar concentrated liquid as a retentate and at the same time recover a sulfuric acid aqueous solution as a permeate; and (4) reusing the whole amount or a part of the sulfuric acid aqueous solution obtained in (3) in the dilute sulfuric acid treatment in (1).

11 Claims, No Drawings

METHOD OF PRODUCING SUGAR LIQUID

TECHNICAL FIELD

This disclosure relates to method of producing a sugar liquid comprising the step of recovering sulfuric acid by using a separation membrane to reuse the sulfuric acid in production of the sugar liquid from cellulose-containing biomass.

BACKGROUND

The process for fermentation production of chemical substances using sugars as raw materials has been used to produce various industrial raw materials. Currently, as sugars to be used as fermentation raw materials, those derived from food materials such as sugar cane and sugar beets are industrially used. However, in view of the fact that a rise in the prices of food raw materials is expected due to future increase in the world population, or in an ethical view of the fact that sugars as industrial materials may compete with sugars for food, it has been a future issue to construct a process of efficiently producing a sugar liquid from a renewable nonfood resource, that is, cellulose-containing biomass, or a process of using the obtained sugar liquid as a fermentation raw material to thereby efficiently convert the obtained sugar liquid to an industrial raw material.

Cellulose-containing biomass are mainly composed of lignin which is an aromatic based polymer product, and cellulose or hemicellulose which are polymer products of monosaccharides. As a representative example of the process of producing a sugar liquid from cellulose-containing biomass, there is an acid treatment in which the cellulose-containing biomass is treated with dilute sulfuric acid. This treatment is a technique that a cellulose fraction is separated from a dilute sulfuric acid-treated liquid containing xylose which is a pentose and the cellulose fraction is further subjected to an enzyme treatment to obtain glucose which is a hexose (A. Aden et al., "Lignocellulosic Biomass to Ethanol Process Design and Economics Utilizing Co-Current Dilute Acid Prehydrolysis and Enzymatic Hydrolysis for Corn Stover," NREL Technical Report (2002)). It has been advancing to scale-up and is said to be a method close to practical use. However, the separation of xylose from sulfuric acid is required for use of the xylose obtained by the dilute sulfuric acid treatment method as a fermentation raw material. In that case, the sulfuric acid is precipitated in a form of calcium sulfate and therefore the cost for waste material and cost involved in reducing environmental load come to be indispensable, which leaves cost reduction as a problem (Journal of Japan Society of Energy and Resources, Vol. 30, No. 5 and AIST TODAY, July Issue, 2009).

For such a problem of reducing the cost of treating sulfuric acid, examples include recovery of sulfuric acid. With regard to the recovery of sulfuric acid, there is disclosed, for example, a method of recovering sulfuric acid from sulfate by electrodialysis with using a bipolar membrane and a cation exchange membrane (Japanese Patent Application Laid-Open Publication No. 5-58601) and a method of employing an anion selective membrane and stripping hydrogen sulfide (Japanese Translation of PCT International Application Publication No. 2008-529946).

When sulfuric acid is recovered from a dilute sulfuric acid-treated liquid containing cellulose-containing biomass according to conventional techniques, there have been problems in that the cost of electricity and expenses for membranes consumed are high; and further the efficiency of recovering sulfuric acid is poor when the concentration of sulfuric acid is low. Therefore, it could be helpful to efficiently recover sulfuric acid in a sugar liquid production process by a dilute sulfuric acid treatment of cellulose-containing biomass.

SUMMARY

We discovered that, by filtering a dilute sulfuric acid-treated liquid obtained by a dilute sulfuric acid treatment of cellulose-containing biomass through a nanofiltration membrane, sulfuric acid to be used in the dilute sulfuric acid treatment can be efficiently recovered.

That is, we provide the following [1] to [5]:

[1] A method of producing a sugar liquid from cellulose-containing biomass, the method comprising the following steps (1) to (4):

step (1): the step of subjecting a cellulose-containing biomass to a dilute sulfuric acid treatment and thereafter separating the treated cellulose-containing biomass into a dilute sulfuric acid-treated liquid and a cellulose-containing solid content;

step (2): the step of adding a cellulase to the cellulose-containing solid content to hydrolyze the cellulose and thereafter obtaining a sugar liquid;

step (3): the step of filtering the dilute sulfuric acid-treated liquid through a nanofiltration membrane at pH 2.5 or lower to thereby separate a sugar concentrated liquid as a retentate and recover a sulfuric acid aqueous solution as a permeate; and step (4): the step of reusing the whole amount or a part of the sulfuric acid aqueous solution obtained in the step (3) in the dilute sulfuric acid treatment in the step (1).

[2] The method of producing a sugar liquid according to [1], which comprises the step of filtering the sulfuric acid aqueous solution obtained in the step (3) through a reverse osmosis membrane to thereby concentrate sulfuric acid as a retentate.

[3] The method of producing a sugar liquid according to [1] or [2], wherein the nanofiltration membrane in the step (3) has a molecular weight cut off of 300 or less.

[4] The method of producing a sugar liquid according to any of [1] to [3], wherein the sulfuric acid aqueous solution comprises one kind or two or more kinds of compounds selected from the group consisting of an organic acid, a furan-based compound, and an aromatic compound.

[5] A method of producing a chemical substance, comprising the step of producing a sugar liquid obtained by the method of producing the sugar liquid according to any of [1] to [4] and the step of culturing a microorganism capable of producing a chemical substance using the thus obtained sugar liquid as a fermentation raw material.

Sulfuric acid can be recovered from the dilute sulfuric acid-treated liquid containing cellulose-containing biomass; and the recovered sulfuric acid is reused in a dilute sulfuric acid treatment of cellulose-containing biomass; and a higher saccharification effect can be surprisingly attained when sulfuric acid recovered is reused in the dilute sulfuric acid treatment of the cellulose-containing biomass, as compared with that of an ordinary dilute sulfuric acid treatment.

DETAILED DESCRIPTION

Our methods will be described in more detail below.

Examples of the cellulose-containing biomass for use in the method of producing a sugar liquid include herbaceous biomass such as bagasse, switchgrass, corn stovers, corncobs, rice straw, or wheat straw; and wood-based biomass such as trees or waste building material. This cellulose-containing biomass contains cellulose or hemicellulose which is polysaccharide formed by dehydration condensation of sugars. Such a polysaccharide can be hydrolyzed to produce a saccharification liquid usable as a fermentation raw material.

The sugar liquid refers to a saccharification liquid obtained by hydrolyzing cellulose-containing biomass. In general, sugars are classified according to the polymerization degree of monosaccharides; and classified in to monosaccharides such as glucose or xylose, oligosaccharide formed by dehydration condensation of two to nine monosaccharides, and further polysaccharides formed by dehydration condensation of 10 or more monosaccharides. The sugar liquid refers to a sugar liquid that contains monosaccharides as a major component; and it specifically contains glucose or xylose as a major component. In addition, the sugar liquid contains oligosaccharides such as cellobiose and monosaccharide such as arabinose or mannose, but in a small amount. The wording "monosaccharides as a major component" means that the monosaccharides account for 80% by weight or more in the total weight of saccharides, namely monosaccharides, oligosaccharides, and polysaccharides that are dissolved in water. As for a concrete method of analyzing monosaccharides, oligosaccharides, and polysaccharides that are dissolved in water, the quantification is feasible by HPLC by comparing to a preparation. As for specific HPLC conditions, no reaction solution is used; Luna $NH_2$ (manufactured by Phenomenex) is used as a column; the mobile phase has a ratio of ultrapure water: acetonitrile=25:75; the flow rate is 0.6 mL/min; the measurement time is 45 min; the detection method is RI (differential refractive index); and the temperature is 30° C.

First, the steps of the method of producing a sugar liquid will be described in detail for each step.

Step (1): The step of subjecting a cellulose-containing biomass to a dilute sulfuric acid treatment and thereafter separating the treated cellulose-containing biomass into a dilute sulfuric acid-treated liquid and a cellulose content Upon a dilute sulfuric acid treatment of cellulose-containing biomass, the cellulose-containing biomass may be subjected, as is, to the dilute sulfuric acid treatment. However, the dilute sulfuric acid treatment can be efficiently carried out by performing a known pretreatment such as grinding, blasting, or hot water prior to the dilute sulfuric acid treatment and, when a cellulose fraction is subjected to an enzyme treatment with cellulase, the efficiency of a hydrolysis reaction by the cellulase improves by the pretreatment. Of the pretreatment, a hydrothermal treatment is a pretreatment of eluting a part of the components of cellulose-containing biomass for easier degradation by boiling with hot water of 50° C. or more and 200° C. or less; and the hydrothermal treatment can remove inorganic ions derived from the cellulose-containing biomass and is thereby preferably employed.

Hydrolysis of the cellulose-containing biomass by the dilute sulfuric acid treatment has a characteristics that the hemicellulose component thereof which is generally low in crystallizability is first hydrolyzed and then the cellulose component thereof which is high in crystallizability is broken down. Therefore, in the hydrolysis by the dilute sulfuric acid treatment, a liquid containing a larger amount of xylose derived from the hemicellulose can be obtained.

The concentration of dilute sulfuric acid at the time of the dilute sulfuric acid treatment is not particularly restricted. It is 0.01 to 20% by weight and preferably 0.1 to 10% by weight. The reaction temperature of the dilute sulfuric acid treatment is 100 to 300° C. and preferably 120 to 250° C. The reaction time thereof is one second to 60 minutes. The number of times that the dilute sulfuric acid treatment is carried out is not particularly restricted. The treatment only need to be carried out once or twice or more. Further, when the dilute sulfuric acid treatment is carried out twice or more, the second or later hydrothermal treatment may be carried out in a condition setting different from that of the first treatment.

The dilute sulfuric acid-treated liquid obtained by the dilute sulfuric acid treatment of the cellulose-containing biomass is a liquid component obtained by separating a liquid in a form of slurry after the dilute sulfuric acid treatment of cellulose-containing biomass, wherein the liquid in a form of slurry is separated into the liquid component and a cellulose-containing solid content; and the dilute sulfuric acid-treated liquid is a liquid containing xylose derived from hemicellulose as a major component. It is to be noted that, when the dilute sulfuric acid treatment is carried out twice or more, the liquid component only need to be recovered from the treated product obtained by repeatedly subjecting the cellulose-containing solid content to the dilute sulfuric acid treatment. Further, the dilute sulfuric acid-treated liquid contains organic acids, furan-based compounds, and aromatic compounds produced as byproducts along the hydrolysis of the cellulose-containing biomass. The ratio between xylose and glucose that are contained in the dilute sulfuric acid-treated liquid are not particularly restricted because, as mentioned above, it varies in treatment conditions including heat and pressure as well as a period of time for the treatment.

Step (2): The step of adding a cellulase to the cellulose-containing solid content to hydrolyze the cellulose and thereafter obtaining a sugar liquid The cellulose-containing solid content obtained by the dilute sulfuric acid treatment of the cellulose-containing biomass is a solid content obtained by separating a liquid in a form of slurry after the dilute sulfuric acid treatment of cellulose-containing biomass, wherein the liquid in a form of slurry is separated into a liquid component and the solid content; and the cellulose-containing solid content has cellulose as a major component and contains a part of hemicellulose and lignin, and a part of organic acids, furan-based compounds, and aromatic compounds which are generated as byproducts along the hydrolysis of the cellulose-containing biomass. For use as a fermentation raw material, the cellulose-containing solid content is hydrolyzed by cellulase which is an enzyme to yield a sugar liquid. The cellulose hydrolyzed by cellulase which is an enzyme or the like is broken down into monosaccharides or oligosaccharides such as glucose or oligosaccharides. The thus obtained sugars are used as fermentation raw materials. It is to be noted that a part of the cellulose-containing solid content may be used, as cellulose, as an industrial raw material such as paper pulp or filter aids.

The above-mentioned cellulase only need to be an enzyme having an activity of degrading cellulose and hemicellulose. In addition to a general cellulase which breaks down cellulose, hemicellulase and xylanase which break down hemicellulose is included. Preferably, it is preferred to be a cellulase comprising an exo-type cellulase or an endo-type cellulase having an activity of degrading crystalline cellulose. As such a cellulase, suitable is cellulase produced by filamentous fungi including the genus *Trichoderma* bacteria and the genus *Acremonium*. The genus *Trichoderma* and the genus *Acremonium* are microorganisms classified as filamentous fungi and are microorganisms that extracellularly secreting a large amount of various kinds of cellulases. The cellulase is preferably cellulase of the genus *Trichoderma*. Further, as an enzyme used in hydrolysis, for the purpose of improving the efficiency of glucose generation, β glucosidase which is an enzyme degrading cellobiose which is oligosaccharide may be added or may be used in the hydrolysis in conjunction with the above cellulase. β glucosidase is not particularly restricted and is preferably one derived from *Aspergillus*. It may be produced by microorganisms such as the genus *Trichoderma* or the genus *Acremonium* by gene recombination. A hydrolysis reaction using such an enzyme is preferably carried out at a pH of around 3 to 7 and more preferably at a pH of around 5. The reaction temperature is preferably 40 to 70° C.

Step (3): The step of filtering the dilute sulfuric acid-treated liquid through a nanofiltration membrane at pH_2.5 or less to separate into a sugar concentrated liquid as a retentate and to separate and recover a sulfuric acid aqueous solution as a permeate In the step (3), sugars (the feed side of the membrane) and sulfuric acid (the permeate side of the membrane) are separated by the nanofiltration membrane. The sulfuric acid aqueous solution which is a permeate of the nanofiltration membrane also contains organic acids, furan-based compounds, and aromatic compounds which are concurrently generated in the acid treatment as they pass through the membrane. On the other hand, by passing sulfuric acid, organic acids, furan-based compounds, and aromatic compounds through the nanofiltration membrane, a ratio thereof in the sugar concentrated liquid recovered from the feed side of the nanofiltration membrane decreases, leading to the sugar concentrated liquid having a higher quality as a fermentation raw material. Further, although it will be detailed in the step (4), reuse of the separated and recovered sulfuric acid aqueous solution in the step (1) enables the amount of sulfuric acid used to be reduced and, in addition, enables the efficiency of hydrolysis of cellulose-containing biomass to improve.

The nanofiltration membrane is a membrane that is also called a nanofilter (nanofiltration membrane, NF membrane) and is in general defined as a "membrane permeating monovalent ions whereas blocking divalent ions." It is a membrane that is thought to have microscopic openings of about several nanometers and mainly used to block fine particles or molecules, ions, salts, or the like in water.

As for materials of the nanofiltration membrane, polymer materials such as cellulose acetate-based polymers, polyamide, polyester, polyimide, or vinyl polymer; or ceramics can be used. The membrane is not limited to a membrane composed of one kind of the above-mentioned material or may be a membrane comprising plural membrane materials. Further, with regard to the membrane structure, the membrane may be either an asymmetric membrane which has a dense layer on at least one side and micropores having pore sizes that gradually increase in the direction from the dense layer toward the inside of the membrane or the other side of the membrane, or a composite membrane which has a very thin functional layer formed by another material on the dense layer of an asymmetric membrane. As the composite membrane, a composite membrane described in Japanese Patent Application Laid-Open Publication No. 62-201606 can be used, which composite membrane has a nanofilter composed of a polyamide functional layer on a support membrane comprising polysulfone as a membrane material.

By filtering the above-mentioned dilute sulfuric acid-treated liquid through the nanofiltration membrane in a condition of pH 2.5 or less, it becomes possible to separate into sugars in the feed side of the membrane and sulfuric acid in the permeate side. While the sugars are blocked by using the nanofiltration membrane and a reverse osmosis membrane, the sugars are not blocked by, for example, an ultrafiltration membrane having the pore diameter larger than that of the nanofiltration membrane and are not concentrated. Further, use of the reverse osmosis membrane does not allow sulfuric acid to be separated in the permeate side of the membrane since the sulfuric acid is concentrated in the feed side with the sugar. That is because, if the pH at the time of the filtration with the nanofiltration membrane is higher than 2.5, sulfuric acid is not separated into the permeate side even when the nanofiltration membrane is used. When the reverse osmosis membrane is used, even if the pH is 2.5 or lower, sugars and sulfuric acid cannot be separated because the sulfuric acid does not pass through the membrane. Further, although the reasons are unknown, the lower the pH value is, the lower permeation of sugars becomes and the higher the concentration efficiency becomes, which leads to a higher efficiency of the separation between the sugar and the sulfuric acid.

Concrete examples of nanofiltration membrane modules include HS5205A and CM10 manufactured by Toyobo Co., Ltd.; NTR-729HF, NTR-7250, NTR-7450, and NTR-7410, which are manufactured by Nitto Denko Corporation; SU610, SU-620, SU-210, and SU-220, which are manufactured by Toray Industries, Inc.; NF-270, NF-200, NF-90, NF-70, NF-45, and NF, which are manufactured by Filmtec; DK series, DL series, HL series, HWS NF series, which are manufactured by DESAL; TS-80 manufactured by TRISEP, MPS-34, MPT-34, MPS-44, MPS-36, MPT-44, which are manufactured by KOCH; and NF97, NF99, and NF99HF, which are manufactured by Alfa Laval.

A mode of the nanofiltration membrane is not particularly restricted. Examples thereof include a spiral type, a tubular type, and a hollow fiber type; and the spiral type is preferably used from the viewpoint of a unit price per module.

In the filtration by the nanofiltration membrane, pressure may be applied. The filtration pressure is preferably 0.1 to 8 MPa. If the filtration pressure is lower than 0.1 MPa, the membrane permeation speed decreases. If the filtration pressure is higher than 8 MPa, it is likely to affect damages of the membrane. Further, if the filtration pressure is 0.5 to 7 MPa, a sugar solution can efficiently permeate because of a high membrane permeation flux.

The molecular weight cut off of the nanofiltration membrane preferably is 300 or less. If it is within this range, it becomes possible to more efficiently separate sugars from sulfuric acid.

The pH of the dilute sulfuric acid-treated liquid at the time of the filtration by the nanofiltration membrane in the step (3) is required to be 2.5 or lower from the viewpoint of the ability of sulfate ion to pass through the nanofiltration membrane, and preferably 2.0 or less at which the ability of sulfate ion to pass through the nanofiltration membrane improves more. The lower limit of the pH of the dilute sulfuric acid-treated liquid is not particularly limited. The lower limit is preferably pH 0.5 or higher and more preferably pH 1.0 or higher. If the pH of the dilute sulfuric acid-treated liquid obtained in the step (1) is 2.5 or lower, the liquid may be as is subjected to a nanofiltration membrane treatment. Further, if the pH of the dilute sulfuric acid-treated liquid exceeds 2.5, the pH may be adjusted as appropriate by adding an acid or alkali to be 2.5 or lower. The acid to be used is not particularly limited. Examples thereof include organic acids such as sulfuric acid, hydrochloric acid, nitric acid, formic acid, and acetic acid. Further, the alkali to be used is not particularly limited either. Preferred examples thereof include ammonia, sodium hydroxide, and potassium hydroxide, which are monovalent alkaline reagents.

If divalent alkaline salts are contained in a dilute sulfuric acid-treated liquid to be subjected to the nanofiltration membrane, the salt does not pass through the nanofiltration membrane and deposits in the liquid in the process of concentrating the liquid, which may cause the fouling of the membrane. Further, if deposits occur at the time of neutralization, an acid corresponding to an amount of the acid that is deposited cannot be recovered. Therefore, when alkaline reagents having a valence of two or more, it is required to decrease the amount of acid or alkali such that the salt deposition does not taken place during the step (3) or to have a system of taking out the deposit in the step (3). When an alkali having a valence of two or more is used, calcium hydroxide is preferred from an aspect of the cost.

Further, it is preferred to remove inorganic ion components from the dilute sulfuric acid-treated liquid to be subjected to the nanofiltration membrane. That is because removal of the inorganic ion component from the dilute sulfuric acid-treated liquid improves the ability of the sulfuric acid to pass through the nanofiltration membrane. A method of removing the inorganic ion component only need to be carried out in the previous step of the step (3) of subjecting the dilute sulfuric acid-treated liquid to the nanofiltration membrane. Examples thereof include a method of subjecting the liquid to an ion-exchange resin and a method of subjecting the liquid to a hydrothermal treatment as a pretreatment of the step (1). Preferred is the method of subjecting the liquid to a hydrothermal treatment prior to the step (1). That is because this method is more attainable at a low cost and a concentration rate of membrane concentration of the liquid can improve when a solid content which is the cellulose-containing solid content obtained in the step (1) is subjected to saccharification.

After the dilute sulfuric acid-treated liquid is filtered through the microfiltration membrane and/or the ultrafiltration membrane, the dilute sulfuric acid-treated liquid is preferably subjected to the nanofiltration membrane. That is because, by carrying out the filtration treatment with the microfiltration membrane and/or the ultrafiltration membrane prior to subjecting the liquid to the nanofiltration membrane, the fouling property of the nanofiltration membrane improves by fine particles in the dilute sulfuric acid-treated liquid. Further, when the pH of the dilute sulfuric acid-treated liquid is adjusted with an acid or alkali, it is rather preferred to carry out the filtration treatment by the above-mentioned microfiltration membrane and/or ultrafiltration membrane after the pH adjustment.

The microfiltration membrane, when used herein, refers to a membrane with an average fine pore diameter of 0.01 μm to 5 mm and is abbreviated as, microfiltration, an MF membrane, or the like. In addition, an ultrafiltration membranes, when used herein, is a membrane with a molecular weight cut off of about 1,000 to 200,000 and is abbreviated as ultrafiltration, a UF membrane, or the like. The pore diameter of the ultrafiltration membrane is so small that it is difficult to measure the fine pore diameter on the membrane surface by an electron microscope or the like; and a value termed as molecular weight cut off, instead of the average fine pore diameter, has been used as an index for the size of pore diameter. The molecular weight cut off refers to one that is well known as an index representing the membrane performance of ultrafiltration membrane, as is described that "a curve obtained by plotting data with the molecular weight of the solute along the horizontal axis and the blocking rate along the vertical axis is called a molecular weight cut off curve; and the molecular weight at which the blocking rate is 90% is called the molecular weight cut off of the membrane." in The Membrane Society of Japan ed., Membrane Experiment Series, Vol. III, Artificial Membrane, edited by Shoji Kimura, Shin-ichi Nakao, Haruhiko Ohya, and Tsutomu Nakagawa (1993 Kyoritsu Shuppan Co., Ltd.), page 92.

Materials of these microfiltration membranes or ultrafiltration membranes are not particularly restricted as long as the material can remove fine particles. Examples thereof include organic materials such as cellulose, cellulose esters, polysulfone, polyether sulfone, chlorinated polyethylene, polypropylene, polyolefin, polyvinyl alcohol, polymethylmethacrylate, polyvinylidene fluoride, or polyethylene tetrafluoride, metals such as stainless steel, and inorganic materials such as ceramic. The material of the microfiltration membrane or the ultrafiltration membrane may be selected as appropriate in light of the characteristics of hydrolysate or running costs. It is preferred to be organic materials; and chlorinated polyethylene, polypropylene, polyvinylidene fluoride, polysulfone, or polyether sulfone is preferred.

Further, prior to the treatment with microfiltration membrane and/or the ultrafiltration membrane, a means for solid-liquid separation by a filtration method, a centrifugal method, or the like may be employed, which means can remove a large portion of solid contents. Examples of the filtration method include filter press, belt filter, belt press, and screw press; and examples of the centrifugal method include screw decanter, De Laval-type centrifuge, or tubular ultracentrifuge.

Step (4): The step of reusing the whole amount or a part of the sulfuric acid aqueous solution obtained in the step (3) in the dilute sulfuric acid treatment in the step (1)

As for the sulfuric acid aqueous solution which is the permeate obtained passing the dilute sulfuric acid-treated liquid through the nanofiltration membrane, the whole amount or a part thereof is reused in the dilute sulfuric acid treatment of the step (1). As shown in the examples, when the solution is reused in the dilute sulfuric acid treatment of the step (1), the yield of the obtained sugars significantly improves. The sulfuric acid aqueous solution also contains, in addition to sulfuric acid, biomass-derived degradation products generated in the dilute sulfuric acid treatment of the step (1) such as organic acids, furan-based compounds, or aromatic compound. Because the use of such a sulfuric acid aqueous solution in the dilute sulfuric acid treatment, even when the dilute sulfuric acid treatment is the same and the acid concentration is the same, improves the efficiency of hydrolyzing a cellulose fraction, it is believed that organic acids, furan-based compounds, or aromatic-based compounds contained in the sulfuric acid aqueous solution, improve the hydrolysis efficiency.

Concrete examples of the organic acid contained in the sulfuric acid aqueous solution include such as formic acid, acetic acid, propionic acid, and butyric acid. Further, examples of the furan-based compound in the sulfuric acid aqueous solution include such as furfural and hydroxymethylfurfural (HMF). These organic acids and furan-based compounds are products of degradation of glucose or xylose which are monosaccharides.

Concrete examples of the phenolic-based compound contained in the sulfuric acid aqueous solution include vanillin, acetovanillin, ferulic acid, coumaric acid, vanillic acid, syringic acid, gallic acid, coniferyl aldehyde, dihydroconiferyl alcohol, hydroquinone, catechol, acetoguaicone, homovanillic acid, 4-hydroxybenzoic acid, and 4-hydroxy-3-methoxyphenyl derivatives (Hibbert's ketones); and these compounds are derived from lignin or lignin precursors.

Further, as for the sulfuric acid aqueous solution to be reused in the step (1), it is preferred to concentrate sulfuric acid prior to the reuse. The sulfuric acid concentration in the sulfuric acid aqueous solution which is the permeate obtained by the nanofiltration membrane is, in principle, a lower value than the concentration of sulfuric acid in the dilute sulfuric acid-treated liquid. Thus, when the permeate of the nanofiltration membrane is reused, as it is, in dilute sulfuric acid treatment, a fresh dilute sulfuric acid is required to be further added; and by concentrating the sulfuric acid aqueous solution, the addition of the fresh dilute sulfuric acid can be reduced. Further, even when the permeate is not used in the dilute sulfuric acid treatment, even when a filtrate obtained by the nanofiltration membrane is not reused as a waste liquid in the dilute sulfuric acid treatment and is treated as the waste liquid, the amount of the waste liquid decreases as compared with that in not treating with the nanofiltration membrane; and there is therefore an effect of drastically reducing labor for waste liquid treatment.

Examples of methods of concentrating the sulfuric acid aqueous solution include such as a distillation method and a reverse osmosis membrane method. Preferred is a method of concentration by a reverse osmosis membrane, that is a method comprising filtering the sulfuric acid aqueous solution through the reverse osmosis membrane to concentrate sulfuric acid in the feed side. The reason why the concentration by the reverse osmosis membrane is preferred is that less energy only need to be used for the concentration as compared to energy in the distillation method, allowing the permeate of the reverse osmosis membrane of the sulfuric acid aqueous solution to be reused as industrial water. The the amount of water used can be markedly decreased in the sugar liquid production process.

The reverse osmosis membrane is a membrane that is also called an RO membrane and is in general defined as a "membrane having a function of blocking salts including monovalent ions." The membrane is a membrane that is believed to have microscopic openings ranging from about several angstroms to several nanometers and mainly used for removing ion components, for example, in desalination of sea water or production of ultrapure water.

As a method of evaluating the performance of the reverse osmosis membrane, the permeation rate (%) of a subject compound (sulfuric acid, monosaccharides, or the like) contained in the saccharification liquid can be calculated for the evaluation. The method of calculating the permeation rate (%) is shown in Equation (1):

Permeation rate (%)=(concentration of subject compound in the permeate side/concentration of subject compound in retentate)×100  (1).

The measuring method of concentration of the subject compound in Equation (1) is not limited as long as an analytical technique that allows highly accurate and reproducible measurement; and high performance liquid chromatography, gas chromatography, or the like can be preferably used. When the subject compound is sulfuric acid, the reverse osmosis membrane preferably has a lower permeation rate thereof. The reverse osmosis membrane is preferably a membrane whose removal rate for sodium chloride is 95% or more. That is because, if it is a membrane having the removal rate of less than 95% the amount of the sulfuric acid lost in the permeate side of the reverse osmosis membrane increases.

Examples of materials of the reverse osmosis membrane include composite membranes with a cellulose acetate-based polymer as a functional layer (hereinafter referred to as cellulose acetate-based reverse osmosis membranes) and composite membranes with polyamide as a functional layer (hereinafter referred to as polyamide-based reverse osmosis membranes). Examples of the cellulose acetate-based polymer include ones that utilize solely organic acid esters of cellulose such as cellulose acetate, cellulose diacetate, cellulose triacetate, cellulose propionate, or cellulose butyrate; or a mixture of these; and a mixed ester. Examples of polyamide include a linear polymer or a cross-linked polymer with aliphatic and/or aromatic diamines as a monomer.

Concrete examples of the reverse osmosis membrane include, in addition to ultra low pressure types SUL-G10 and SUL-G20, and low pressure types SU-710, SU-720, SU-720F, SU-710L, SU-720L, SU-720LF, SU-720R, SU-710P, and SU-720P, which are polyamide-based reverse osmosis membrane modules manufactured by Toray Industries, Inc.; high pressure types containing UTC80 as a reverse osmosis membrane SU-810, SU-820, SU-820L, and SU-820FA; cellulose acetate-based reverse osmosis membranes SC-L100R, SC-L200R, SC-1100, SC-1200, SC-2100, SC-2200, SC-3100, SC-3200, SC-8100, and SC-8200, which are manufactured by the same company; NTR-759HR, NTR-729HF, NTR-70SWC, ES10-D, ES20-D, ES20-U, ES15-D, ES15-U, and LF10-D, which are manufactured by Denko Corporation; RO98pHt, RO99, HR98PP, and CE4040C-30D, which are manufactured by Alfa Laval; GE Sepa manufactured by GE, BW30-4040, TW30-4040, XLE-4040, LP-4040, LE-4040, SW30-4040, and SW30HRLE-4040, which are manufactured by Filmtec; TFC-HR and TFC-ULP, which are manufactured by KOCH; and ACM-1, ACM-2, and ACM-4, which are manufactured by TRISEP.

A reverse osmosis membrane having a polyamide material is preferably used. That is because when a cellulose acetate-based membrane is used over an extended time period, the enzyme used in a previous step, in particular, a part of cellulase components may permeate to break down cellulose which is a membrane material.

As for the membrane form of the reverse osmosis membrane, ones in an appropriate form such as a flat sheet membrane type, a spiral type, or a hollow fiber type can be used.

In the filtration by the reverse osmosis membrane, pressure may be applied. The filtration pressure is preferably 0.1 to 8 MPa. If the filtration pressure is lower than 0.1 MPa, the membrane permeation speed decreases. If the filtration pressure is higher than 8 MPa, it is likely to affect damages of the membrane. Further, if the filtration pressure is 0.5 to 7 MPa, a filtrate can be efficiently permeated from the sulfuric acid aqueous solution because of a high membrane permeate flux. Next, methods of producing a chemical substance will be described, which methods use, as a fermentation raw material, a purified sugar liquid obtained by the method of producing a sugar liquid.

By using a purified sugar liquid obtained as a fermentation raw material, chemical substances can be produced. The purified sugar liquid obtained contains, as a major component, glucose and/or xylose, which are carbon sources for the growth of microorganisms or cultured cells. On the other hand, the contents of fermentation inhibitors such as furan compounds, organic acids, or aromatic compounds are very small, and therefore the purified sugar liquid can be effectively used as a fermentation raw material, in particular as a carbon source.

Examples of microorganisms or cultured cells for use in the method of producing a chemical substance include yeasts such as baker's yeast, bacteria such as *Escherichia coli* or coryneform bacteria, filamentous fungi, actinomycetes, animal cells, and insect cells, all of which are commonly used in the fermentation industry. The microorganism or cells to be used may be ones isolated from the natural environment or may be ones whose characteristics is partially modified by mutation or gene recombination. In particular, because a sugar liquid derived from a cellulose-containing biomass contains pentoses such as xylose, a microorganism having enhanced metabolic pathways for pentoses can be preferably used.

As for a medium for use in the method of producing a chemical substance, used preferably is a liquid medium containing as appropriate, in addition to the purified sugar liquid, nitrogen sources, inorganic salts, and, as necessary, organic trace nutrients such as amino acids or vitamins. The purified sugar liquid contains, as carbon sources, monosaccharides which can be used by microorganisms such as glucose or xylose. In some cases, sugars such as glucose, sucrose, fructose, galactose, or lactose; starch saccharification liquid containing these sugars; sweet potato molasses; sugar beet molasses; high test molasses; organic acids such as acetic acid; alcohols such as ethanol; glycerin; or the like may be further added as carbon sources to use as fermentation raw materials. As for the nitrogen source, used are ammonia gas, aqueous ammonia, ammonium salts, urea, nitrates, and other organic nitrogen sources which are supplementarily used such as oilcakes, soybean-hydrolyzed liquid, casein digests, other amino acids, vitamins, corn steep liquor, yeast or yeast extracts, meat extract, peptides such as peptone, various fermentation bacterial cells and hydrolysates thereof, or the like. As for the inorganic salt, phosphates, magnesium salts, calcium salts, iron salts, manganese salts, or the like can be added as appropriate.

If the microorganism requires a particular nutrient for its growth, the nutrient substance only need to be added as a preparation or a natural product containing it. Further, an antifoaming agent may be used as necessary.

The culture of the microorganism is usually carried out at pH 4 to 8 and a temperature of 20 to 40° C. The pH of a culture liquid is adjusted to a predetermined value usually at pH 4 to 8 by an inorganic or organic acid, an alkaline material, as well as urea, calcium carbonate, ammonia gas, or the like. If the feeding rate of oxygen need to be increased, means can be employed, the means involve keeping an oxygen concentration an oxygen at 21% or higher by adding air, applying pressure to the culture, increasing a stirring speed, or increasing an volume of aeration.

As methods of producing a chemical substance using, as a fermentation raw material, the purified sugar liquid obtained by the method of producing a sugar liquid, known methods of fermentation culture may be employed. A continuous culture method disclosed in WO 2007/097260 is preferably employed from the viewpoint of the productivity.

The chemical substance produced by the method of producing a chemical substance are not limited as long as it is a substance produced by the above microorganisms or cells in the culture liquid. Concrete examples of the produced chemical substance can include substances produced in a large scale in the fermentation industry such as alcohols, organic acids, amino acids, or nucleic acids. Examples of the alcohol include ethanol, 1,3-propanediol, 1,4-butanediol, and glycerol; examples of the organic acid include acetic acid, lactic acid, pyruvic acid, succinic acid, malic acid, itaconic acid, and citric acid; examples of the nucleic acid include nucleosides such as inosine or guanosine and nucleotides such as inosinic acid or guanylic acid; and diamine compounds such as cadaverine. Further, our methods can be applied to production of substances such as enzymes, antibiotics, or recombinant proteins.

EXAMPLES

By way of example, our methods of producing a sugar liquid will be further described in detail below. This disclosure is, however, not limited thereto.

Reference Example 1: Measurement of the Concentration of Inorganic Ions

The concentration of cations and anions was quantified in the HPLC condition shown below by comparing with a standard sample. Sulfate ion was quantified by this anion analysis.
1) Analysis of Anions
Column: Ion Pac AS22 (manufactured by DIONEX)
Mobile phase: 4.5 mM $Na_2CO_3$/1.4 mM $NaHCO_3$ (flow rate 1.0 mL/min)
Reaction solution: none
Detection method: electrical conductivity (with a suppressor being used)
Temperature: 30° C.
2) Analysis of Cations
Column: Ion Pac CS12A (manufactured by DIONEX)
Mobile phase: 20 mM methanesulfonic acid (flow rate 1.0 mL/min)
Reaction solution: none
Detection method: electrical conductivity (with a suppressor being used)
Temperature: 30° C.

Reference Example 2: Method of Analyzing the Concentration of Monosaccharides

The concentration of monosaccharides that was contained in the obtained liquid was quantified in HPLC conditions described below by comparing to a standard sample.
Column: Luna $NH_2$ (manufactured by Phenomenex)
Mobile phase: ultrapure water:acetonitrile=25:75 (flow rate 0.6 mL/min)
Reaction solution: none
Detection method: RI (differential refractive index)
Temperature: 30° C.

Reference Example 3: Method of Analyzing Furan-Based Compounds and Aromatic-Based Compounds Furan-based compounds (HMF and furfural) and phenolic-based compounds (vanillin, coumaric acid, and ferulic acid) which were contained in the liquid were quantified in the HPLC conditions described below by comparing to a standard sample.
Column: Synergi HidroRP 4.6 mm×250 mm (manufactured by Phenomenex)
Mobile phase: acetonitrile—0.1% $H_3PO_4$ (flow rate 1.0 mL/min)
Detection method: UV (283 nm)
Temperature: 40° C.

Reference Example 4: Method of Analyzing Organic Acids

Organic acids (acetic acid, formic acid) contained in the liquid were quantified in the HPLC conditions described below by comparing with a standard sample.
Column: Shim-Pack SPR-H and Shim-Pack SCR101H (manufactured by Shimadzu Corporation) in series
Mobile phase: 5 mM p-toluenesulfonic acid (flow rate 0.8 mL/min)
Reaction solution: 5 mM p-toluenesulfonic acid, 20 mM bis tris, 0.1 mM EDTA.2Na (flow rate 0.8 mL/min)
Detection method: electrical conductivity
Temperature: 45° C.

Reference Example 5: Composition Analysis of Biomass

By reference to the LAP method published by NREL ("Determination of Structural Carbohydrates and Lignin in Biomass, Laboratory Analytical Procedure (LAP)"), the composition was analyzed by the following method.

An appropriate amount of a sample was aliquoted; and with regard to the water content, the sample was kept at a temperature of 120° C. using an infrared moisture meter (manufactured by Kett Electric Laboratory, FD-720); and a value obtained from a difference between a stable value after evaporation and an initial value was measured. Thereafter, the obtained dried sample was subjected to ignition at a temperature of 600° C. to determine the ash content thereof.

Further, the sample was transferred to a stainless steel vat and air-dried in the laboratory atmosphere to be roughly in the equilibrium state; and the resultant was ground by a Wiley mill and passed through a sieve to adjust its particle size to about 200 to 500 μm. The sample after this adjustment was dried in vacuum at a temperature of 60° C.; and the content of each component on an absolute dry base was determined by correcting absolute dry mass. To a beaker, 0.3 g of this sample for analysis was measured by a scale balance; and 3 mL of sulfuric acid with a concentration of 72% was added thereto and left to stand, while occasionally stirred, at a temperature of 30° C. for one hour. This reaction solution was completely transferred to a pressure bottle with 84 mL of purified water and then autoclaved for thermolysis at a temperature of 120° C. for one hour. After the thermolysis, a degraded liquid and residue were filtered out and added to a filtrate and a washing liquid of residues to make a constant volume of 100 mL. The resultant was used as a test liquid. Further, sugar recovery standards test using monosaccharides was simultaneously carried out at the time of thermolysis for the purpose of correcting excessive breakdown of sugars. With regard to the monosaccharide (xylose, arabinose, mannose, glucose, and galactose) in the test liquid, quantification was carried out by a high-speed liquid chromatography method (GL-7400 manufactured by GL Sciences Inc., fluorescence detection). From the monosaccharide concentration of the obtained degraded liquid and the amount of the sample broken down, the amount of constitutive sugars in the sample was determined.

By the sugar recovery standards test of monosaccharide, the amount of constitutive sugars was determined. Using a sugar excessive breakdown correction coefficient at the time of thermolysis (Sf: survival factor), the amount of the constitutive sugars was corrected. It is to be noted that because lignin and the like are present in addition to the above-mentioned components, summation of the proportion for all of the above-mentioned items does not give 100%.

Example 1

Rice straw was used as cellulose-containing biomass. The composition analysis of rice straw was analyzed by the method of Reference Example 5 to bring about the result in Table 1. The rice straw was ground by rotating in a state of a screen mesh diameter of 3 mm at 420 rpm in a rotary cutter mill RCM-400 type (manufactured by Nara Machinery Co., Ltd.). Subsequently, the ground rice straw 0.15 kg (dry weight) was submerged in 1% sulfuric acid aqueous solution 1.5 L as a dilute sulfuric acid treatment and subjected to treatment by an autoclave (manufactured by Nitto Koatsu Co., Ltd.) at 150° C. for 10 minutes. After the dilute sulfuric acid treatment, solid-liquid separation was carried out to separate into a dilute sulfuric acid-treated liquid (hereinafter saccharification liquid A) which is a liquid component and a cellulose-containing solid content. The pH of the saccharification liquid A was 1.0 and the composition analysis of the cellulose-containing solid content brought about the result in Table 1.

Further, an ammonium solution was added to the cellulose-containing solid content. The pH thereof was adjusted to around 5 and the solid concentration thereof was adjusted to 10%. To this liquid, "Accellerase DUET (registered trademark)" (manufactured by Danisco Japan) was added as an enzyme. A hydrolysis reaction was carried out while stirring and mixing at 50° C. for one day. Thereafter, filter press was carried out by using a filter press MO-4 (manufactured by Yabuta Industries Co., Ltd.). Undegraded cellulose or lignin was separated and removed to obtain saccharification liquid B. The turbidity of the saccharification liquid B was 9 NTU. The concentration of inorganic salts contained in the saccharification liquid A and the saccharification liquid B, and the composition of monosaccharides, organic acids, furan-based compounds, and aromatic compounds are each as shown in Table 2.

TABLE 1

Composition analysis of rice straw and cellulose-containing solid content after dilute sulfuric acid treatment

| Analysis item | Unit | Rice straw (before dilute sulfuric acid treatment) | After dilute sulfuric acid treatment |
|---|---|---|---|
| Xylose | % · dry | 17.2 | 4.2 |
| Arabinose | % · dry | 3.2 | 0.4 |
| Mannose | % · dry | 0.3 | 0.1 |
| Glucose | % · dry | 35.6 | 62.1 |
| Galactose | % · dry | 2.0 | 0.3 |
| Ash content | % · dry | 12.0 | 0.3 |

TABLE 2

Composition of saccharification liquid

| Analysis item | Unit | Saccharification liquid A | Saccharification liquid B |
|---|---|---|---|
| Glucose | g/L | 2.5 | 45.6 |
| Xylose | g/L | 20.2 | 3.23 |
| Formic acid | g/L | 0 | 0.2 |
| Acetic acid | g/L | 3.5 | 0.1 |
| HMF | g/L | 0.2 | 0 |
| Furfural | g/L | 1.8 | 0.1 |
| Coumaric acid | g/L | 0.3 | 0 |
| Sulfuric acid | g/L | 9.5 | 0.2 |

TABLE 2-continued

Composition of saccharification liquid

| Analysis item | Unit | Saccharification liquid A | Saccharification liquid B |
|---|---|---|---|
| Phosphoric acid | g/L | Not detected | 0.68 |
| Potassium | g/L | 2.5 | 0.4 |
| Ammonia | g/L | Not detected | 1.4 |
| Sodium | g/L | 0.5 | 0.3 |

Next, 2 L of permeate obtained by filtering the saccharification liquid A through a microfiltration membrane with a pore diameter of 0.22 μm (hereinafter referred to as dilute sulfuric acid-treated MF liquid) was each prepared and filtered through nanofiltration membranes 1 to 3 (nanofiltration membrane 1: MPS-34 manufactured by KOCH (molecular weight cut off: 200), nanofiltration membrane 2: UTC60 manufactured by Toray Industries, Inc. (molecular weight cut off: 300), and nanofiltration membrane 3: NTR-7410 manufactured by Nitto Denko Corporation (molecular weight cut off: 700)). As for the filtration by the nanofiltration membrane, the nanofiltration membrane was cut out to a flat sheet membrane to be placed in "SEPA CF II" manufactured by GE Osmonics (active membrane area: 140 cm$^2$) and then placed therein. Filtration was carried out for 1.5 L of each dilute sulfuric acid-treated MF liquid at a feed rate of 2 L/min and a filtration rate of 5.0 mL/min. The composition of the permeate (sulfuric acid aqueous solution) and the retentate (sugar concentrated liquid) are shown in Tables 3 and 4.

TABLE 3

Composition of permeate

| Analysis item | Unit | Nanofiltration membrane 1 | Nanofiltration membrane 2 | Nanofiltration membrane 3 |
|---|---|---|---|---|
| Glucose | g/L | 0.1 | 0.2 | 0.7 |
| Xylose | g/L | 0.8 | 1.8 | 8.2 |
| Formic acid | g/L | Not detected | Not detected | Not detected |
| Acetic acid | g/L | 3.0 | 3.6 | 3.5 |
| HMF | g/L | 0.1 | 0.2 | 0.2 |
| Furfural | g/L | 1.8 | 1.9 | 1.9 |
| Coumaric acid | g/L | 0.1 | 0.2 | 0.3 |
| Sulfuric acid | g/L | 6.7 | 7.1 | 7.0 |
| Potassium | g/L | 2.0 | 2.0 | 2.0 |
| Sodium | g/L | 0.4 | 0.4 | 0.4 |

TABLE 4

Composition of retentate

| Analysis item | Unit | Nanofiltration membrane 1 | Nanofiltration membrane 2 | Nanofiltration membrane 3 |
|---|---|---|---|---|
| Glucose | g/L | 9.7 | 9.4 | 7.9 |
| Xylose | g/L | 78.4 | 75.4 | 56.2 |
| Formic acid | g/L | Not detected | Not detected | Not detected |
| Acetic acid | g/L | 3.0 | 3.2 | 3.5 |
| HMF | g/L | 0.5 | 0.2 | 0.2 |
| Furfural | g/L | 1.8 | 1.5 | 1.5 |
| Coumaric acid | g/L | 0.9 | 0.6 | 0.3 |
| Sulfuric acid | g/L | 17.9 | 16.7 | 17.0 |
| Potassium | g/L | 4.0 | 4.0 | 4.0 |
| Sodium | g/L | 0.8 | 0.8 | 0.8 |

Further, concentrated sulfuric acid was added to the obtained permeate of the nanofiltration membrane 1 such that the dilute sulfuric acid concentration came to be 1%; and the ground rice straw 0.15 kg (dry weight) was put into 1.5 L of this liquid and subjected to treatment by an autoclave (manufactured by Nitto Koatsu Co., Ltd.) at 150° C. for 10 minutes. After the treatment, solid-liquid separation was carried out and a cellulose-containing solid content was separated. The composition analysis of the cellulose-containing solid content by the method of Reference Example 5 brought about the result in Table 5. Further, an ammonium solution was added to the cellulose-containing solid content; and the pH thereof was adjusted to around 5 and the solid concentration thereof was adjusted to 10%. The resulting liquid was, in the same manner as described above, added with "Accellerase DUET (registered trademark)" (manufactured by Danisco Japan) and stirred and mixed at 50° C. for one day to carry out the hydrolysis reaction. Filter press was carried out by using a filter press MO-4 (manufactured by Yabuta Industries Co., Ltd.) to obtain saccharification liquid C. The composition of sulfate ion, monosaccharides, organic acids, furan-based compounds, aromatic compounds contained in the saccharification liquid C is as shown in Table 6. When compared to the composition of the saccharification liquid B in Table 1, the concentration of glucose and xylose clearly improved. From the above, we found that, by utilizing the sulfuric acid aqueous solution recovered as the permeate of the nanofiltration membrane in the dilute sulfuric acid treatment of the cellulose-containing biomass, a saccharification rate of the cellulose-containing solid content by cellulase at the later stage improved.

TABLE 5

Composition analysis of cellulose-containing solid content after reuse dilute sulfuric acid treatment

| Analysis item | Unit | After reuse dilute sulfuric acid treatment |
|---|---|---|
| Xylose | % · dry | 5.2 |
| Arabinose | % · dry | 0.3 |
| Mannose | % · dry | 0.1 |
| Glucose | % · dry | 68.3 |
| Galactose | % · dry | 0.2 |
| Ash content | % · dry | 0.2 |

TABLE 6

Composition of saccharification liquid C

| Analysis item | Unit | Saccharification liquid C |
|---|---|---|
| Glucose | g/L | 56.2 |
| Xylose | g/L | 4.12 |
| Formic acid | g/L | 0.3 |
| Acetic acid | g/L | 0.3 |
| HMF | g/L | 0.3 |
| Furfural | g/L | 0.2 |
| Coumaric acid | g/L | 0.1 |
| Sulfuric acid | g/L | 0.3 |
| Phosphoric acid | g/L | 0.7 |
| Potassium | g/L | 0.4 |
| Ammonia | g/L | 1.6 |
| Sodium | g/L | 0.3 |

Example 2

The pH of the dilute sulfuric acid-treated MF liquid of Example 1 was adjusted to pH 1.5, 2.0, and 2.5 using ammonia; and 1.5 L out of 2 L of each liquid was filtered with nanofiltration membranes 1 to 3. The composition of the resulting permeate is shown in Tables 7 to 9.

TABLE 7

Case of using nanofiltration membrane 1

| Analysis item | Unit | pH_1.5 | pH_2.0 | pH_2.5 |
|---|---|---|---|---|
| Glucose | g/L | 0.1 | 0.1 | 0.2 |
| Xylose | g/L | 0.8 | 0.9 | 1.2 |
| Formic acid | g/L | Not detected | Not detected | Not detected |
| Acetic acid | g/L | 3.0 | 3.0 | 3.0 |
| HMF | g/L | 0.1 | 0.1 | 0.2 |
| Furfural | g/L | 1.8 | 1.8 | 1.9 |
| Coumaric acid | g/L | 0.1 | 0.1 | 0.0 |
| Sulfuric acid | g/L | 5.7 | 5.0 | 3.1 |
| Potassium | g/L | 2.0 | 2.0 | 2.0 |
| Sodium | g/L | 0.4 | 0.4 | 0.4 |

TABLE 8

Case of using nanofiltration membrane 2

| Analysis item | Unit | pH_1.5 | pH_2.0 | pH_2.5 |
|---|---|---|---|---|
| Glucose | g/L | 0.2 | 0.2 | 0.4 |
| Xylose | g/L | 1.8 | 1.9 | 2.3 |
| Formic acid | g/L | Not detected | Not detected | Not detected |
| Acetic acid | g/L | 3.6 | 3.6 | 3.6 |
| HMF | g/L | 0.2 | 0.2 | 0.2 |
| Furfural | g/L | 1.9 | 1.9 | 1.9 |
| Coumaric acid | g/L | 0.2 | 0.2 | 0.1 |
| Sulfuric acid | g/L | 5.5 | 4.8 | 2.8 |
| Potassium | g/L | 2.0 | 2.0 | 2.0 |
| Sodium | g/L | 0.4 | 0.4 | 0.4 |

TABLE 9

Case of using nanofiltration membrane 3

| Analysis item | Unit | pH_1.5 | pH_2.0 | pH_2.5 |
|---|---|---|---|---|
| Glucose | g/L | 0.7 | 0.8 | 1.0 |
| Xylose | g/L | 8.2 | 8.2 | 8.5 |
| Formic acid | g/L | Not detected | Not detected | Not detected |
| Acetic acid | g/L | 3.5 | 3.5 | 3.5 |
| HMF | g/L | 0.2 | 0.2 | 0.2 |
| Furfural | g/L | 1.9 | 1.9 | 1.9 |
| Coumaric acid | g/L | 0.3 | 0.3 | 0.2 |
| Sulfuric acid | g/L | 5.7 | 4.9 | 3.1 |
| Potassium | g/L | 2.5 | 2.5 | 2.5 |
| Sodium | g/L | 0.5 | 0.5 | 0.5 |

Comparative Example 1

The pH of the dilute sulfuric acid-treated MF liquid of Example 1 was adjusted to pH 3.0 and 5.0 using ammonia; and 1.5 L out of 2 L of each liquid was filtered with nanofiltration membranes 1 to 3. The composition of the resulting permeate is shown in Tables 10 to 12. In Comparative Example 1, as compared to Example 2, the permeability of the nanofiltration membrane for sulfuric acid remarkably decreased and sulfuric acid was not able to be recovered. In addition, the blocking rate for sugars also decreased.

TABLE 10

Case of using nanofiltration membrane 1

| Analysis item | Unit | pH_3.0 | pH_5.0 |
|---|---|---|---|
| Glucose | g/L | 0.4 | 0.5 |
| Xylose | g/L | 1.6 | 1.8 |
| Formic acid | g/L | Not detected | Not detected |
| Acetic acid | g/L | 3.0 | 1.7 |
| HMF | g/L | 0.2 | 0.2 |
| Furfural | g/L | 1.9 | 1.9 |
| Coumaric acid | g/L | 0.0 | 0.0 |
| Sulfuric acid | g/L | 0.5 | 0.0 |
| Potassium | g/L | 2.0 | 2.0 |
| Sodium | g/L | 0.4 | 0.4 |

TABLE 11

Case of using nanofiltration membrane 2

| Analysis item | Unit | pH_3.0 | pH_5.0 |
|---|---|---|---|
| Glucose | g/L | 0.5 | 0.6 |
| Xylose | g/L | 2.5 | 3.0 |
| Formic acid | g/L | Not detected | Not detected |
| Acetic acid | g/L | 3.6 | 2.5 |
| HMF | g/L | 0.2 | 0.2 |
| Furfural | g/L | 1.9 | 1.9 |
| Coumaric acid | g/L | 0.1 | 0.1 |
| Sulfuric acid | g/L | 0.7 | 0.0 |
| Potassium | g/L | 2.0 | 2.0 |
| Sodium | g/L | 0.4 | 0.4 |

TABLE 12

Case of using nanofiltration membrane 3

| Analysis item | Unit | pH_3.0 | pH_5.0 |
|---|---|---|---|
| Glucose | g/L | 1.0 | 1.2 |
| Xylose | g/L | 8.6 | 9.2 |
| Formic acid | g/L | Not detected | Not detected |
| Acetic acid | g/L | 3.5 | 3.2 |
| HMF | g/L | 0.2 | 0.2 |
| Furfural | g/L | 1.9 | 1.9 |
| Coumaric acid | g/L | 0.1 | 0.1 |
| Sulfuric acid | g/L | 0.6 | 0.3 |
| Potassium | g/L | 2.5 | 2.5 |
| Sodium | g/L | 0.5 | 0.5 |

Comparative Example 2

The dilute sulfuric acid-treated MF liquid of Example 1 (pH 1.0) was aliquoted to 2 L; and 1.5 L of each was filtered with a ultrafiltration membrane GE series of a molecular weight cut off of 1,000 manufactured by GE or a reverse osmosis membrane UTC80 manufactured by Toray Industries, Inc. The composition of the resulting retentate is shown in Tables 13 and 14. When the ultrafiltration membrane was used, a large amount of sugars ended up passing through into the permeate side. On the other hand, when the reverse osmosis membrane was used, sugars was able to be blocked in the retentate side but sulfuric acid was also blocked, thereby failing to separate the sugar from sulfuric acid, which disabled the recovery of the sulfuric acid aqueous solution.

TABLE 13

Use of ultrafiltration membrane

| Analysis item | Unit | Permeate | Retentate |
| --- | --- | --- | --- |
| Glucose | g/L | 1.9 | 4.3 |
| Xylose | g/L | 19.5 | 22.3 |
| Formic acid | g/L | Not detected | Not detected |
| Acetic acid | g/L | 3.5 | 3.5 |
| HMF | g/L | 0.2 | 0.2 |
| Furfural | g/L | 1.9 | 1.9 |
| Coumaric acid | g/L | 0.3 | 0.3 |
| Sulfuric acid | g/L | 9.2 | 10.4 |
| Potassium | g/L | 2.5 | 2.5 |
| Sodium | g/L | 0.5 | 0.5 |

TABLE 14

Use of reverse osmosis membrane

| Analysis item | Unit | Permeate | Retentate |
| --- | --- | --- | --- |
| Glucose | g/L | 0.0 | 10.0 |
| Xylose | g/L | 0.2 | 80.2 |
| Formic acid | g/L | Not detected | Not detected |
| Acetic acid | g/L | 0.3 | 13.1 |
| HMF | g/L | 0.0 | 0.8 |
| Furfural | g/L | 0.3 | 6.3 |
| Coumaric acid | g/L | 0.0 | 1.2 |
| Sulfuric acid | g/L | 0.2 | 37.4 |
| Potassium | g/L | 0.0 | 10.0 |
| Sodium | g/L | 0.0 | 2.0 |

Example 4

With regard to the step of hydrolyzing the cellulose-containing biomass of the step (1), when hydrothermal treatment is carried out as a pretreatment to remove inorganic salt substances derived from cellulose-containing biomass, 0.1 to 10% by weight of dilute sulfuric acid treatment is thereafter carried out and a hydrolysis of the cellulose-containing biomass is carried out using cellulase will be described.

Rice straw was used as cellulose-containing biomass. The rice straw was ground by rotating in a state of a screen mesh diameter of 3 mm in a rotary cutter mill RCM-400 type (manufactured by Nara Machinery Co., Ltd.). Subsequently, the ground rice straw 0.15 kg (dry weight) was submerged in water 1.5 L and subjected to treatment by an autoclave (manufactured by Nitto Koatsu Co., Ltd.) at 150° C. for 10 minutes. After the treatment, solid-liquid separation was carried out to separate into steamed water which is a liquid component and hydrothermally-treated cellulose which corresponds to the solid content. The composition of monosaccharides, organic acids, furan-based compounds, aromatic compounds in the steamed water, and salt concentration thereof are as shown in Table 15.

TABLE 15

Composition of steamed water

| Analysis item | Unit | Steamed water |
| --- | --- | --- |
| Glucose | g/L | Not detected |
| Xylose | g/L | Not detected |
| Formic acid | g/L | Not detected |
| Acetic acid | g/L | Not detected |
| HMF | g/L | Not detected |

TABLE 15-continued

Composition of steamed water

| Analysis item | Unit | Steamed water |
| --- | --- | --- |
| Furfural | g/L | 0.2 |
| Coumaric acid | g/L | 0.3 |
| Sulfuric acid | g/L | Not detected |
| Potassium | g/L | 2.5 |
| Sodium | g/L | 0.5 |

Next, hydrothermally-treated cellulose 0.15 kg (dry weight) was submerged in dilute sulfuric acid aqueous solution 1.5 L with a dilute sulfuric acid concentration of 1.0% by taking the water content of the hydrothermally-treated cellulose-containing solid content into consideration and subjected to treatment by an autoclave (manufactured by Nitto Koatsu Co., Ltd.) at 150° C. for 10 minutes. After the dilute sulfuric acid treatment, solid-liquid separation was carried out to separate into a dilute sulfuric acid-treated liquid (hereinafter, saccharification liquid D) and a cellulose-containing solid content. The composition of monosaccharides, organic acids, furan-based compounds, aromatic compounds contained in the saccharification liquid D and the salt concentration thereof are as shown in Table 16. By carrying out the hydrothermal treatment as a pretreatment of the dilute sulfuric acid treatment, the sugar concentration improved and concurrently the concentration of inorganic salts decreased.

TABLE 16

Composition of saccharification liquid D

| Analysis item | Unit | Saccharification liquid D |
| --- | --- | --- |
| Glucose | g/L | 2.7 |
| Xylose | g/L | 22.1 |
| Formic acid | g/L | 0 |
| Acetic acid | g/L | 3.6 |
| HMF | g/L | 0.1 |
| Furfural | g/L | 1.8 |
| Coumaric acid | g/L | 0 |
| Sulfuric acid | g/L | Not detected |
| Potassium | g/L | 0 |
| Sodium | g/L | 0 |

Further, the saccharification liquid D was filtered through a microfiltration membrane of a pore diameter of 0.22 μm; and the obtained permeate 2 L was filtered through a nanofiltration membrane 1 (MPS-34 manufactured by KOCH). As for the filtration by the nanofiltration membrane, the nanofiltration membrane was cut out to a flat sheet membrane to be placed in "SEPA CF II" manufactured by GE Osmonics (active membrane area: 140 cm$^2$) and then placed therein; and the filtration was carried out for 1.5 L of the permeate at a feed rate of 2 L/min and a filtration rate of 5.0 mL/min. The composition of the obtained permeate of the nanofiltration membrane is as shown in Table 17. We found that, by carrying out the hydrothermal treatment as a pretreatment of the dilute sulfuric acid treatment, the property of removing sulfuric acid improved. This was presumably because the concentration of inorganic ions and the like contained in the dilute sulfuric acid-treated liquid decreased.

TABLE 17

Permeate composition of nanofiltration membrane 1

| Analysis item | Unit | Permeate |
|---|---|---|
| Glucose | g/L | 0.2 |
| Xylose | g/L | 1 |
| Formic acid | g/L | 0 |
| Acetic acid | g/L | 3.3 |
| HMF | g/L | 0.1 |
| Furfural | g/L | 1.8 |
| Coumaric acid | g/L | 0 |
| Sulfuric acid | g/L | 7.8 |
| Potassium | g/L | 0 |
| Sodium | g/L | 0 |

Example 5

Two liters of permeate of the nanofiltration membrane 1 obtained in Example 1 were prepared and 1.0 L of the permeate was filtered through a flat sheet membrane of reverse osmosis membrane SW2540 manufactured by Filmtec at a feed rate of 2 L/min and a filtration rate of 5.0 mL/min. The composition of 1.0 L of the retentate and 1.0 L of the permeate is as shown in Table 18. The sulfuric acid was barely lost and was able to be concentrated.

TABLE 18

Result of retentate permeate composition of reverse osmosis membrane treatment

| Analysis item | Unit | Concentrated liquid | Filtrate |
|---|---|---|---|
| Glucose | g/L | 0.2 | 0.0 |
| Xylose | g/L | 1.5 | 0.1 |
| Formic acid | g/L | Not detected | Not detected |
| Acetic acid | g/L | 5.9 | 0.1 |
| HMF | g/L | 0.2 | 0.0 |
| Furfural | g/L | 3.6 | 0.0 |
| Coumaric acid | g/L | 0.2 | 0.0 |
| Sulfuric acid | g/L | 13.2 | 0.2 |
| Potassium | g/L | 4.0 | 0.0 |
| Sodium | g/L | 0.8 | 0.0 |

The retentate of the reverse osmosis membrane was diluted with RO water to make 1.5 L such that the concentration of sulfuric acid came to be 1.0%; and the ground rice straw 0.15 kg (dry weight) was put thereinto and subjected to treatment by an autoclave (manufactured by Nitto Koatsu Co., Ltd.) at 150° C. for 10 minutes. After the treatment, solid-liquid separation was carried out and a cellulose-containing solid content was separated. Subsequently, an ammonium solution was added to the cellulose-containing solid content; and the pH thereof was adjusted to around 5 and the solid concentration thereof was adjusted to 10%. This resulting liquid was, in the same manner as described above, added with "Accellerase DUET (registered trademark)" (manufactured by Danisco Japan) and stirred and mixed at 50° C. for one day to carry out the hydrolysis reaction; and further the filter press was carried out by using a filter press MO-4 (manufactured by Yabuta Industries Co., Ltd.) to obtain saccharification liquid E. The composition of sulfate ion, monosaccharides, organic acids, furan-based compounds, and aromatic compound contained in the saccharification liquid E is as shown in Table 19; and, by carrying out the dilute sulfuric acid treatment using the reverse osmosis membrane concentrated liquid of the sulfuric acid aqueous solution, the saccharification rate to glucose and xylose improved, as compared with that of the saccharification liquid B in Table 2. Further, in the composition analysis of cellulose-containing solid content after the reuse dilute sulfuric acid treatment by the method of Reference Example 5, it was found that the proportion of glucose composing cellulose in particular increased.

TABLE 19

Result of composition of Saccharification liquid E

| Analysis item | Unit | Saccharification liquid E |
|---|---|---|
| Glucose | g/L | 60.3 |
| Xylose | g/L | 4.3 |
| Formic acid | g/L | 0.3 |
| Acetic acid | g/L | 0.4 |
| HMF | g/L | 0.3 |
| Furfural | g/L | 0.2 |
| Coumaric acid | g/L | 0.2 |
| Sulfuric acid | g/L | 0.4 |
| Phosphoric acid | g/L | 0.7 |
| Potassium | g/L | 0.6 |
| Ammonia | g/L | 1.6 |
| Sodium | g/L | 0.4 |

TABLE 20

Composition analysis of cellulose-containing solid content after reuse dilute sulfuric acid treatment

| Analysis item | Unit | After reuse dilute sulfuric acid treatment |
|---|---|---|
| Xylose | % · dry | 5.4 |
| Arabinose | % · dry | 0.0 |
| Mannose | % · dry | 0.1 |
| Glucose | % · dry | 70.2 |
| Galactose | % · dry | 0.1 |
| Ash content | % · dry | 0.2 |

Example 6

Ethanol fermentation by genetically-modified *Escherichia coli* (KO11 strain, ATCC55124) was carried out by using the sugar liquid of Example 1 as a fermentation raw material. As for the sugar liquid, the sugar concentrated liquid of nanofiltration membrane 1 of Example 1 (hereinafter, saccharification liquid F) and a liquid mixture obtained by mixing 4 L of the saccharification liquid B with 1 L of the saccharification liquid F (hereinafter, saccharification liquid G) were used. Note that the liquid composition of the saccharification liquid G was as shown in Table 21.

TABLE 21

Composition of saccharification liquid G

| Analysis item | Unit | Saccharification liquid G |
|---|---|---|
| Glucose | g/L | 38.4 |
| Xylose | g/L | 18.2 |
| Formic acid | g/L | 0.16 |
| Acetic acid | g/L | 0.68 |
| HMF | g/L | 0.1 |
| Furfural | g/L | 0.44 |
| Coumaric acid | g/L | 0.18 |
| Sulfuric acid | g/L | 3.7 |
| Potassium | g/L | 1.1 |
| Sodium | g/L | 0.4 |

The genetically-modified *Escherichia coli* described above was first pre-cultured in a YPDX medium (1% glucose, 1% xylose, 1% yeast extract (Bacto Yeast Extract, manufactured by BD), 2% polypeptone (manufactured by Nihon Pharmaceutical Co., Ltd.) at 32° C. for one day. Subsequently, the saccharification liquid F and the saccharification liquid G were adjusted with calcium hydroxide (manufactured by Wako Pure Chemical Industries, Ltd.) to have pH 6.0; and thereafter the obtained culture liquid was added in 10% by volume. After added, the recombinant *Escherichia coli* was incubated at 32° C. for two days. The cumulative concentration of ethanol contained in the culture liquid obtained by this operation was quantified by a gas chromatography. Shimadzu GC-2010 capillary GC TC-1 (GL science) 15 meter L.*0.53 mm I.D., df 1.5 µm was used. Detection and calculation were carried out by a flame ionization detector for evaluation. As a result, we confirmed that ethanol was obtained in 20.1 g/L from the saccharification liquid F and in 12.9 g/L from the saccharification liquid G. That is, we confirmed that the production of ethanol, which is a chemical substance, could be produced by using the sugar liquid obtained as a fermentation raw material.

Example 7

L-lactic acid fermentation by *Lactococcus lactis* JCM7638 strain was carried out by using the saccharification liquid F or the saccharification liquid G as a fermentation raw material. *Lactococcus lactis* JCM7638 strain was subjected to static culture at a temperature of 37° C. for 24 hours. The concentration of L-lactic acid contained in the culture liquid was analyzed in the condition below. The microorganism described above was pre-cultured in a YPDX medium (1% glucose, 1% xylose, 1% yeast extract (Bacto Yeast Extract/BD), 2% polypeptone (manufactured by Nihon Pharmaceutical Co., Ltd.) at 37° C. for one day. Subsequently, the saccharification liquid F and the saccharification liquid G were adjusted with calcium hydroxide (manufactured by Wako Pure Chemical Industries, Ltd.) to have pH 6.0; and thereafter the obtained culture liquid was added in 10% by volume. After added, the microorganism was incubated at 37° C. for two days. The cumulative concentration of lactic acid contained in the culture liquid obtained by this operation was analyzed by the method of Reference Example 4. As the result of the analysis, we confirmed that L-lactic acid was accumulated in 47.8 g/L from the saccharification liquid F and in 30.5 g/L from the saccharification liquid G. We confirmed that the production of L-lactic acid, which is a chemical substance, is feasible by using the sugar liquid obtained as a fermentation raw material.

INDUSTRIAL APPLICABILITY

The sugar liquid obtained by the method of producing a sugar liquid can be used as a fermentation raw material for various chemical substance.

The invention claimed is:
1. A method of producing a sugar liquid from cellulose-containing biomass comprising (1) to (4):
   (1) subjecting a cellulose-containing biomass to a dilute sulfuric acid treatment and thereafter separating the treated cellulose-containing biomass into a dilute sulfuric acid-treated liquid and a cellulose-containing solid content;
   (2) adding a cellulase to the cellulose-containing solid content to hydrolyze the cellulose and thereafter obtaining a sugar liquid;
   (3) filtering the dilute sulfuric acid-treated liquid through a nanofiltration membrane at pH 2.5 or lower to thereby separate a sugar concentrated liquid as a retentate and recover a sulfuric acid aqueous solution as a permeate; and
   (4) reusing the whole amount or a part of the sulfuric acid aqueous solution obtained in (3) in the dilute sulfuric acid treatment in (1).

2. The method according to claim 1, further comprising filtering the sulfuric acid aqueous solution obtained in (3) through a reverse osmosis membrane to thereby concentrate sulfuric acid as a retentate.

3. The method according to claim 1, wherein the nanofiltration membrane in (3) has a molecular weight cut off of 300 or less.

4. The method according to claim 1, wherein the sulfuric acid aqueous solution comprises one kind or two or more kinds of compounds selected from the group consisting of an organic acid, a furan-based compound, and an aromatic compound.

5. A method of producing a chemical substance comprising producing a sugar liquid obtained by the method according to claim 1 and culturing a microorganism capable of producing a chemical substance using the sugar liquid thus obtained as a fermentation raw material.

6. The method according to claim 2, wherein the nanofiltration membrane in (3) has a molecular weight cut off of 300 or less.

7. The method according to claim 2, wherein the sulfuric acid aqueous solution comprises one kind or two or more kinds of compounds selected from the group consisting of an organic acid, a furan-based compound, and an aromatic compound.

8. The method according to claim 3, wherein the sulfuric acid aqueous solution comprises one kind or two or more kinds of compounds selected from the group consisting of an organic acid, a furan-based compound, and an aromatic compound.

9. A method of producing a chemical substance comprising producing a sugar liquid obtained by the method according to claim 2 and culturing a microorganism capable of producing a chemical substance using the sugar liquid thus obtained as a fermentation raw material.

10. A method of producing a chemical substance comprising producing a sugar liquid obtained by the method according to claim 3 and culturing a microorganism capable of producing a chemical substance using the sugar liquid thus obtained as a fermentation raw material.

11. A method of producing a chemical substance comprising producing a sugar liquid obtained by the method according to claim 4 and culturing a microorganism capable of producing a chemical substance using the sugar liquid thus obtained as a fermentation raw material.

* * * * *